United States Patent [19]

Diefenbach et al.

[11] Patent Number: 4,918,254

[45] Date of Patent: Apr. 17, 1990

[54] NICKEL CATALYZED DISPLACEMENT REACTION

[75] Inventors: Steven P. Diefenbach; Gene C. Robinson, both of Baton Rouge, La.

[73] Assignee: Ethyl Corporation, Richmond, Va.

[21] Appl. No.: 306,512

[22] Filed: Feb. 6, 1989

[51] Int. Cl.$^4$ ............... C07C 5/00; C07C 6/00; C07C 2/88
[52] U.S. Cl. .................. 585/328; 585/637; 556/187; 556/190
[58] Field of Search ............. 585/328, 637; 556/190, 556/187

[56] References Cited

U.S. PATENT DOCUMENTS

| | | | |
|---|---|---|---|
| 3,391,175 | 7/1968 | Davis | 260/448 |
| 3,391,219 | 7/1968 | Davis et al. | 260/683.15 |
| 3,657,301 | 4/1972 | Motz | 556/190 |
| 3,784,623 | 1/1974 | Motz | 585/637 |
| 3,829,520 | 8/1974 | Ferrell | 585/637 |

FOREIGN PATENT DOCUMENTS 906744  9/1962  United Kingdom .

OTHER PUBLICATIONS

Ziegler, "Brennstoff-Chemie", Heft No. 21/22, pp. 321–325, Nov. 17, 1954.
Fischer et al., "Angewandte Chemie," 12, No. 12, Dec. 1973, pp. 943–953.
Poe et al., "Symposium on Production and Use of Alpha Olefins", Division of Petroleum Chemistry, Am. Chem. Soc.

*Primary Examiner*—H. M. S. Sneed
*Assistant Examiner*—J. Saba
*Attorney, Agent, or Firm*—Joseph D. Odenweller

[57] ABSTRACT

Alkyl groups in trialkyl aluminum are displaced by α-olefins in the presence of a nickel catalyst. The displaced alkyl group evolve as α-olefins. The displacement is fast and the catalyst is then poisoned with a catalyst poison such as lead to prevent undesired side reactions such as isomerization of α-olefins to internal olefins or dimerization to vinylidene olefins.

20 Claims, No Drawings

NICKEL CATALYZED DISPLACEMENT REACTION

BACKGROUND

It has long been known that nickel catalyzes the displacement of a butyl group as butene from a butyl aluminum by ethylene (K. Ziegler, Brennstoff Chem., 35, 321 (1954)). The mechanism of this catalysis has been extensively studied (K. Fischer et al. "Angewandte Chemie" 12 No. 12 pages 943–953 (December 1973)). It has been proposed that the trialkyl aluminum reduces the nickel compound to Ni metal which reacts with the α-olefin to form an olefin complex which reacts with trialkyl aluminum to displace the alkyls bonded to aluminum in an equilibrium reaction.

The nickel catalyzed alkyl displacement has not achieved commercial significance because the catalyst is extremely difficult to remove from the product and its presence causes undesirable side reactions. These side reactions are reverse displacement, isomerization and branched chain formation (Poe et al., Symposium on Production and Use of Alpha Olefins, Div. of Petrol. Chem., Am. Chem. Soc., Los Angeles, Mar.31–Apr.5, 1963). Poe et al. attempted to circumvent this problem by using a heterogenous catalyst system with nickel deposited on a support such as alumina. They reported high initial displacement activity which sharply declined after 4–8 hours and could not be reactivated.

Davis et al., U.S. Pat. No. 3,391,219, resorted to non-catalytic thermal displacement of alkyls of trialkyl aluminum with α-olefins. Displacement temperatures in the range of 280°–320° C. were required to effect the displacement followed by rapid cooling to about 120° C. to minimize isomerization and other side reactions of the effluent α-olefin stream. Although very effective, this process suffers from the high energy consumption required by the high displacement temperature followed by the rapid cooling.

From the above it can be seen that a need exists for a process that can take advantage of the low temperature displacement temperatures made possible by the use of nickel catalysts while avoiding the undesirable side reactions encountered in the past with the use of nickel catalysts.

SUMMARY

It has now been discovered that the nickel catalyzed trialkyl aluminum displacement reaction can be conducted without any substantial amount of side reactions such as isomerization or dimerization by permitting the displacement to proceed only until it is about at equilibrium and then adding a catalyst poison in an amount sufficient to deactivate the nickel catalyst.

DESCRIPTION OF THE PREFERRED EMBODIMENTS

A preferred embodiment of the invention is a process for displacing alkyl groups from a first trialkyl aluminum or mixture thereof, said process comprising contacting said first trialkyl aluminum or mixture thereof with an α-olefin or mixture thereof containing a different distribution of carbon atoms than the alkyl groups in said first trialkyl aluminum or mixture thereof, in the presence of a nickel catalyst at a temperature of about $-10°$ to 150° C. whereby said α-olefins displace at least part of the alkyl groups in said first trialkyl aluminum or mixture thereof to form a second trialkyl aluminum or mixture thereof, further characterized by adding a deactivating amount of a catalyst poison selected from lead and copper and compounds thereof which are capable of deactivating said nickel catalyst after the displacement reaction has substantially reached equilibrium but before any significant isomerization of the α-olefins to internal olefins has occurred.

The process is operable with any trialkyl aluminum including those containing alkyl groups of 2 to 30 or more carbon atoms including mixtures of different trialkyl aluminum compounds and also trialkyl aluminum compounds containing different alkyl groups in a single molecule. Some examples are triethyl aluminum, tri-n-propyl aluminum, tri-isobutyl aluminum, tri-n-hexyl aluminum, tri-n-octyl aluminum, tri-n-dodecyl aluminum, tri-n-tetradecyl aluminum, tri-n-hexadecyl aluminum, tri-n-eicosyl aluminum, tri-n-docosanyl aluminum, tri-n-tricosyl aluminum, diethyl n-butyl aluminum, ethyl butyl hexyl aluminum, n-decyl n-dodecyl n-tetradecyl aluminum and the like including mixtures thereof. Aluminum hydrides and alkyl aluminum hydrides are known to inhibit the displacement reaction so the trialkyl aluminum should not contain any significant amount of hydride although it need not be hydride-free.

In a preferred mode of operation the trialkyl aluminum is a mixture of trialkyl aluminums generated in an ethylene chain growth process for making α-olefins as described in Davis et al. U.S. Pat. No. 3,391,219 incorporated herein by reference. The displacement reaction as used in that process results in peaking of the more needed α-olefins. Since the trialkyl aluminums in the process result from ethylene chain growth, the alkyl groups will contain an even number of carbon atoms. Triethyl aluminum in the effluent from the displacement reaction is distilled and recycled to the feed for the chain growth reaction. As a result, the resultant stream will consist essentially of trialkyl aluminum compounds in which the alkyl groups contain from 4–30 carbon atoms and have an even number of carbon atoms.

The α-olefin stream used in the displacement reaction can be any α-olefin stream such as those containing 2–30 carbon atoms such as ethylene, propylene, 1-butene, 1-hexene, 1-octene, 1-decene, 1-dodecene, 1-tetradecene, 1-hexadecene, 1-octadecene, 1-eicosene, 1-triacontene and the like including mixtures thereof. The α-olefin stream may include vinylidene, internal and tri-substituted olefin diluents. When used as part of the chain growth process as described in Davis et al. the α-olefin stream will be primarily one or more α-olefins of even carbon number from 4 to about 30, more preferably from 4 to about 16. In one preferred embodiment the displacing olefin is ethylene. In another highly preferred embodiment the displacing olefin is 1-butene and the first trialkyl aluminum is a tri-$C_{2-30}$ alkyl aluminum. In still another preferred embodiment the displacing olefin stream comprises mainly 1-butene, 1-hexene, 1-octene or 1-decene or mixtures of 2 or more of such olefins and the first trialkyl aluminum is a tri-$C_{4-16}$ alkyl aluminum. In still another preferred embodiment the displacing olefin stream comprises mainly 1-dodecene, 1-tetradecene or 1-hexadecene or mixtures of 2 or more of such olefins and the first trialkyl aluminum is a tri-$C_{4-10}$ alkyl aluminum.

In order to achieve any useful result, the composition of the displacing olefin stream must be different than the composition of the alkyl groups bonded to aluminum in the first trialkyl aluminum stream fed to the displacement. If the molar amount of each individual α-olefin in the olefin feed is the same as the equivalents of each alkyl group in the first trialkyl aluminum, the displacement product referred to as the second trialkyl aluminum will be the same as the first trialkyl aluminum. For example, if the α-olefin is 25 mole percent 1-butene, 25 mole percent 1-hexene and 50 mole percent 1-octene, and the first trialkyl aluminum stream is a random mixture containing 25 mole percent n-butyl groups, 25 mole percent n-hexyl groups and 50 mole percent n-octyl groups, then the product or second trialkyl aluminum will have about the same composition, based on alkyl groups, as the first trialkyl aluminum. This should be avoided since it does not accomplish anything useful.

The amount of α-olefin should be in stoichiometric excess over the amount required to replace all alkyl groups. Preferably the amount of α-olefin should be at least a 200 percent excess over the stoichiometric amount required to replace all alkyl groups. Still more preferably the α-olefin feed should be at least a 500 percent stoichiometric excess over the first trialkyl aluminum. In this manner, since the displacement reaction is an equilibrium reaction, the alkyl substitution in the second trialkyl aluminum will more closely approach the distribution of the α-olefin feed.

Any nickel catalyst can be used that has at least some solubility in the displacement reaction system or which reacts with the reaction mixture to form nickel-containing catalyst having at least some solubility. Investigators in this area still differ as to what the actual nickel catalyst is that exists in the system and catalyzes the reaction. However, knowledge of what the catalyst species is is not necessary to successfully carry out the new process.

In a highly preferred embodiment, the nickel is added in the form of a soluble nickel compound such as nickel naphthenate, nickel bis(acetylacetonate), nickelocene, bis(1,5-cyclooctadiene)nickel, nickel bis(N-alkyl salicylaldimino) and the like.

The amount of nickel required to catalyze the reaction is very low, on the order of parts per million (ppm). A useful range is about 1–100 parts by weight nickel per million parts of reaction mixture. A preferred range is about 2–20 ppm. A more preferred catalyst concentration is about 2–10 ppm.

The process is operable over a wide temperature range. However, one of the main advantages of the nickel catalyzed process over the non-catalyzed process is the capability of operating at low to moderate temperatures. For example Davis et al. disclose the non-catalytic displacement reaction carried out at 280°–320° C. followed by a rapid cool down to avoid side reactions. The nickel catalyzed process proceeds at temperatures down to 15° C. or lower. There is no real upper limit as the react rate increases with temperature. As a practical matter, the preferred temperature range is about −10° to 150° C., more preferably 10°–65° C. and especially about 20°–35°0 C. This results in a much more energy efficient process compared to the non-catalytic process.

Both displacement and side reactions (e.g. isomerization, dimerization, chain growth) proceed concurrently. However the displacement reaction rate is much higher than the rate of the side reactions. This permits termination of the displacement reaction after a time that allows it to go substantially to completion and before a time in which the side reactions, especially isomerization, become significant. By "significant" is meant that the amount of undesired by-products formed does not exceed an amount which would render the olefin effluent stream unsuitable for its intended purpose. In general the α-olefin product should contain less than 25 weight percent newly formed combined internal, tri-substituted and vinylidene olefins. More preferably the α-olefin product should not exceed 20 weight percent newly formed combined internal, tri-substituted and vinylidene olefins. The preferred α-olefin product is at least 80 weight percent and more preferably 85 weight percent vinyl α-olefin and more preferably at least 90 weight percent vinyl α-olefin based on the tri-n-alkylaluminum converted. The process is capable of making α-olefin product that is at least 95 weight percent vinyl α-olefin based on tri-n-alkylaluminum converted.

Since all rates vary with temperature and amount of catalyst, the optimum time for termination under each specific condition will require a minimal amount of experimentation. In general when operating at 25° C., the reaction should be terminated after a reaction period of about 30 seconds to 1 hour. A preferred reaction time is 1.75–2.25 minutes. At higher temperatures, e.g. 50°–100° C., the preferred reaction time before side reactions become significant will be shorter.

When the displacement has proceeded to the desired extent, usually reaction equilibrium, a catalyst poison is added in an amount that will deactivate the nickel catalyst and prevent undesirable side reactions. These include lead and copper and compounds thereof. Suitable lead compounds are lead naphthenate, lead acetylacetonate, lead 2-ethylhexanoate, tetraethyl lead, etc. Suitable copper compounds are copper naphthenate, copper acetylacetonate, cuprous bromide, cuprous 2-ethylhexanoate and the like. Use of the metals as the catalyst poison requires the metals to be in very finely divided forms and requires a greater amount of the catalyst poison. For example, amorphous lead metal was an effective catalyst poison at a Pb/Ni atom ratio of about 500. The catalyst poisons which are effective at the lowest concentrations have been lead compounds, e.g. lead naphthenate, lead 2-ethylhexanoate and lead acetylacetonate.

The amount of catalyst poison should be an amount that effectively inhibits all undesired side reactions. With lead compounds a lead/nickel atom ratio of 1.0 has been effective and even lower amounts may be effective. Hence a useful Pb/Ni atom ratio is about 0.5/1.0 to 5.0/1.0.

After the catalyst poison has been added, second trialkyl aluminum product can be recovered by conventional methods such as distillations. When lead compounds are used as the poison, nickel and at least part of the lead form a precipitate which can be removed by filtration.

The following examples show how the displacement reaction is carried out and the results that can be achieved.

EXAMPLES 1–10

In a 6 dram vial fitted with a magnetic stirrer was placed a mixture of 1-hexene (except where noted) and tri-n-octyl aluminum (TNOA) at the mole ratio given in Table I. To this was added a heptane solution of nickel (II) naphthenate (except for Example 4 which used a heptane solution of nickel bis(15-cyclooctadiene)) in an amount to provide the amount of Ni in ppm shown in Table I. This mixture was stirred at the temperature and time given in Table I. At that exact time a heptane solution of lead (II) naphthenate was syringed into the reaction mixture in Examples 2-3 and 5-10 to give the Pb/Ni atom ratio shown in Table I. Lead (II) 2-ethylhexanoate was used in Example 4. No lead poison was added to Example I which serves as a comparative example.

TABLE I

| Example No. | 1-hexene/TNOA Mole Ratio | Catalyst[1] Conc. | Temp °C./ Time | Pb/Ni Atom Ratio |
|---|---|---|---|---|
| 1 | 11.3 | 10.5 | 25°/2 min | none |
| 2 | 11.3 | 10.5 | 25°/30 sec | 2.0 |
| 3 | 11.1 | 10.8 | 25°/2 min | 2.0 |
| 4 | 11.8 | 9.1 | 25°/2 min | 2.0 |
| 5 | 10.5 | 10.3 | 25°/2 min | 0.5 |
| 6 | 10.7 | 3.2 | 65°/30 sec | 2.0 |
| 7 | 10.7 | 3.3 | 65°/30 sec | 2.0 |
| 8 | 10.1[2] | 10.1 | 25°/2 min | 2.0 |
| 9 | 10.9[3] | 10.5 | 25°/30 sec | 2.0 |
| 10 | 4 | 9.9 | 100°/2 min | 2.0 |

[1]Parts by weight Ni per million parts mixture.
[2]Olefin was 1-tetradecene.
[3]Trialkyl aluminum was tri-n-butylaluminum.
[4]Displacement olefin was ethylene at 225 psig in place of 1-hexene with 5.7 milimoles of TNOA.

The results for each example are given in Table II.

TABLE II

| Example | % $R_3Al$ Conversion | | Olefin Composition[1] (Area Percent) | | | |
|---|---|---|---|---|---|---|
| | | | Initial | At End of Rx | | After Stirring at Rx Temp |
| 1 | 74 | Vi | 97.1 | 96.1 | | 1.2[2] |
| | | Int | 1.4 | 2.3 | | 95.6 |
| | | Tri | 0.2 | 0.2 | | 1.7 |
| | | Vd | 1.3 | 1.4 | | 1.4 |
| 2 | 43.2[3] | | | | | |
| 3 | 72.4 | Vi | 97.7 | — | | 97.4[4] 97.3[5] |
| | | Int | 1.2 | — | | 1.4 1.6 |
| | | Tri | 1.1 | — | | 1.2 1.2 |
| | | Vd | <0.2 | — | | <0.2 <0.2 |
| 4 | 75.8 | Vi | 96.7 | 96.2 | 95.9[4] | 96.3[6] 96.1[7] |
| | | Int | 2.4 | 2.8 | 3.0 | 2.7 2.7 |
| | | Tri | <0.5 | <0.5 | <0.5 | <0.5 <0.5 |
| | | Vd | 0.8 | 1.0 | 1.0 | 1.0 1.1 |
| 5 | 72.0 | Vi | 96.7 | — | 96.6[8] | 96.1[6] 96.2[5] |
| | | Int | 2.4 | — | 2.4 | 2.6 2.5 |
| | | Tri | <0.5 | — | 0.5 | 0.8 0.9 |
| | | Vd | 0.8 | — | 0.5 | 0.5 0.4 |
| 6 | 73.6 | Vi | 96.8 | — | | 95.5[9] 95.2[10] |
| | | Int | 2.4 | — | | 3.5 3.7 |
| | | Tri | <0.5 | — | | <0.5 <0.5 |
| | | Vd | 0.8 | — | | 1.0 1.1 |
| 7 | 70.0 | Vi | 98.0 | — | | 96.6[9] 97.6[11] |
| | | Int | 0.7 | — | | 1.4 1.4 |
| | | Tri | 0.7 | — | | 1.1 0.6 |
| | | Vd | 0.6 | — | | 0.8 0.4 |
| 8 | 74.5 | Vi | 86.1 | — | | 85.7[13] 85.9[7] |
| | | Int | 5.5 | — | | 6.1 6.0 |
| | | Tri | n.d.[12] | — | | n.d. n.d. |
| | | Vd | 8.3 | — | | 8.2 8.2 |
| 9 | 32.0 | 14 | | | | |
| 10 | 94.4 | Vi | — | — | 93.4[4] | 93.3[15] |
| | | Int | — | — | | 4.2 4.3 |
| | | Tri | — | — | | 0.9 0.9 |
| | | Vd | — | — | | 1.5 1.5 |

[1]Vi = Vinyl olefin, Int. = Internal Olefin, Tri = Tri-substituted olefin, Vd = Vinylidene olefin.
[2]18 hours without Pb poison.
[3]Conversion 5 min. after addition of Pb poison - 44.2% after 18 hr - 45.8%, after 24 hours - 45.4%, after 42 hours - 45.7%.
[4]5 minutes after addition of Pb poison.
[5]18 hours after addition of Pb poison.
[6]1 hour after addition of Pb poison.
[7]72 hours after addition of Pb poison.
[8]4 minutes after addition of Pb poison.
[9]1 minute at 65° C. after addition of Pb poison.
[10]2 hours at 65° C. after addition of Pb poison.
[11]Distilled at 25° C./0.1 Torr.
[12]n.d. = not detected.
[13]1 minute after addition of Pb poison.
[14]Conversion 5 minutes after addition of Pb poison - 34%, after 10 minutes-35%, after 72 hours - 35%.
[15]4 days after addition of Pb poison.

Example 1 shows that at 25° C. over a 2-minute period 1-hexene converts 74 percent of the TNOA forming an olefin product that is (by gas chromatography) 96.1 area percent vinyl olefin (i.e. R—CH=$CH_2$), 2.3 area percent internal olefin (i.e. R—CH=CH—R), 0.2 area percent tri-substituted olefin (i.e. RRC=CHR) and 1.3 area percent vinylidene olefin (i.e. R—C(=$CH_2$)—R). However on standing 18 hours with the nickel catalyst the vinyl content dropped dramatically to only 1.2 area percent while internals increased to 95.6 area percent. This is why the nickel catalyzed displacement reaction has been of little use in displacing alkyl groups from trialkyl aluminum ($R_3Al$) to form a different α-olefin. While the displacement goes fast, the new α-olefin rapidly isomerizes to internal olefins.

Example 2 shows that after 30 seconds at 25° C., 43.2 percent of the initial TNOA is converted to a different $R_3Al$ by 1-hexene displacement. As shown in footnote 3, this percent conversion remains almost constant through 42 hours showing that the Pb has deactivated the Ni catalyst.

Example 3 shows a 72.4 percent $R_3Al$ conversion after 2 minutes at 25° C. to an initial olefin product that is 97.7% vinyl, 1.2% internal, 1.1% tri-substituted and <0.2% vinylidene. The significant feature here is that 5 minutes and 18 hours after the end of the displacement reaction and injection of the Pb poison, the olefin composition remained almost constant. In fact vinyl olefin content decreased only 0.4% over 18 hours at 25° C.

The remaining examples show the same high conversion to a vinyl olefin-rich product that remains essentially unisomerized over a long period due to the injection of the Pb catalyst poison.

Example 10 is worth special notice for showing that ethylene converts 94.4 percent of the TNOA after 2 minutes at 100° C. to a high α-olefin product which remains substantially unchanged 4 days after the end of the displacement and injection of the Pb solution.

The above results show that the new process makes the known nickel catalyzed trialkyl aluminum displacement reaction extremely useful for alkyl displacement to produce a different α-olefin product that does not isomerize or dimerize on standing.

We claim:
1. A process for displacing alkyl groups from a first trialkyl aluminum or mixture thereof, said process comprising contacting said first trialkyl aluminum or mix- ture thereof with an α-olefin or mixture thereof containing a different distribution of carbon atoms than the alkyl groups in said first trialkyl aluminum or mixture thereof, in the presence of a nickel catalyst at a temperature of about −10° to 150° C. whereby said α-olefins displace at least part of the alkyl groups in said first trialkyl aluminum or mixture thereof to form a second trialkyl aluminum or mixture thereof, further characterized by adding a deactivating amount of a catalyst poison selected from lead and compounds thereof which are capable of deactivating said nickel catalyst after the displacement reaction has proceeded to the desired extent but before any significant isomerization of the α-olefins to internal olefins has occurred.

2. A process of claim 1 wherein said nickel catalyst provides about 1–100 parts by weight nickel per million parts of reaction mixture.

3. A process of claim 1 wherein said α-olefin is ethylene and said first trialkyl aluminum is a trialkyl aluminum or mixture thereof in which the alkyl groups contain an even number of carbon atoms from 4 to 30.

4. A process of claim 1 wherein said α-olefin is 1-butene and said first trialkyl aluminum is a trialkyl aluminum or mixture thereof wherein the alkyl groups contain a even number of carbon atoms in the range of 2 to 30.

5. A process of claim 1 wherein said α-olefin is an olefin stream comprising mainly 1-butene, 1-hexene, 1-octene and 1-decene and said first trialkyl aluminum is a mixture of trialkyl aluminum wherein the alkyl groups in said trialkyl aluminum contain an even number of carbon atoms from 4 to about 16.

6. A process of claim 1 wherein said α-olefin is an olefin stream comprising 1-dodecene, 1-tetradecene or 1-hexadecene or mixtures of 2 or more of said α-olefins and said first trialkyl aluminum is a mixture of trialkyl aluminum wherein the alkyl groups in said trialkyl aluminum contain an even number of carbon atoms from 4 to about 10.

7. A process of claim 1 wherein said α-olefin or mixtures thereof is at least 200% in excess of the stoichiometric amount required to replace all alkyl groups of said first trialkyl aluminum or mixtures thereof whereby the alkyl group distribution of said second trialkyl aluminum or mixture thereof corresponds substantially to the α-olefin distribution of said α-olefin or mixture thereof.

8. A process of claim 5 wherein said α-olefin or mixture thereof is at least 500 percent in excess of the stoichiometric amount required to replace all alkyl groups of said first trialkyl aluminum or mixture thereof.

9. A process of claim 1 wherein said catalyst poison is a lead compound which is at least partially soluble in the reaction mixture.

10. A process of claim 9 wherein said lead compound is lead naphthenate, lead acetylacetonate or lead 2-ethylhexanoate or mixtures thereof.

11. A process of claim 9 wherein said nickel catalyst is a nickel compound which is at least partially soluble in the reaction mixture and is used in an amount to provide about 1–100 parts by weight of nickel per million parts of reaction mixture.

12. A process of claim 11 wherein said nickel compound is nickel naphthenate, nickel bis-acetylacetonate, bis(1,5-cyclooctadiene)nickel, nickel bis(N-alkyl salicylaldimino).

13. A process of claim 12 wherein said nickel compound provides about 2–20 parts by weight nickel per million parts of reaction mixture.

14. A process of claim 11 wherein said lead compound is lead naphthenate, lead acetylacetonate or lead 2-ethylhexanoate or mixtures thereof.

15. A process of claim 14 wherein said α-olefin is ethylene and said first trialkyl aluminum is a trialkyl aluminum or mixture thereof wherein the alkyl groups contain an even number of carbon atoms from 4 to 30.

16. A process of claim 14 wherein said α-olefin is 1-butene and said first trialkyl aluminum is a trialkyl aluminum or mixture thereof wherein the alkyl groups contain an even number of carbon atoms in the range of 2 to 30.

17. A process of claim 14 wherein said α-olefin is an olefin stream comprising mainly 1-butene, 1-hexene, 1-octene and 1-decene and said first trialkyl aluminum is a mixture of trialkyl aluminum wherein the alkyl groups contain an even number of carbon atoms from 4 to about 16.

18. A process of claim 14 wherein said α-olefin is an olefin stream comprising 1-dodecene, 1-tetradecene or 1-hexadecene or mixtures of 2 or more of said α-olefins and said first trialkyl aluminum is a mixture of trialkyl aluminum wherein the alkyl groups in said trialkyl aluminum contain an even number of carbon atoms from 4 to about 10.

19. A process of claim 11 wherein said lead compound is added in an amount to provide about 0.5–2.0 atoms of lead per atom of nickel.

20. A process of claim 1 wherein said catalyst poison finely divided metallic lead.

* * * * *